Figure 1:
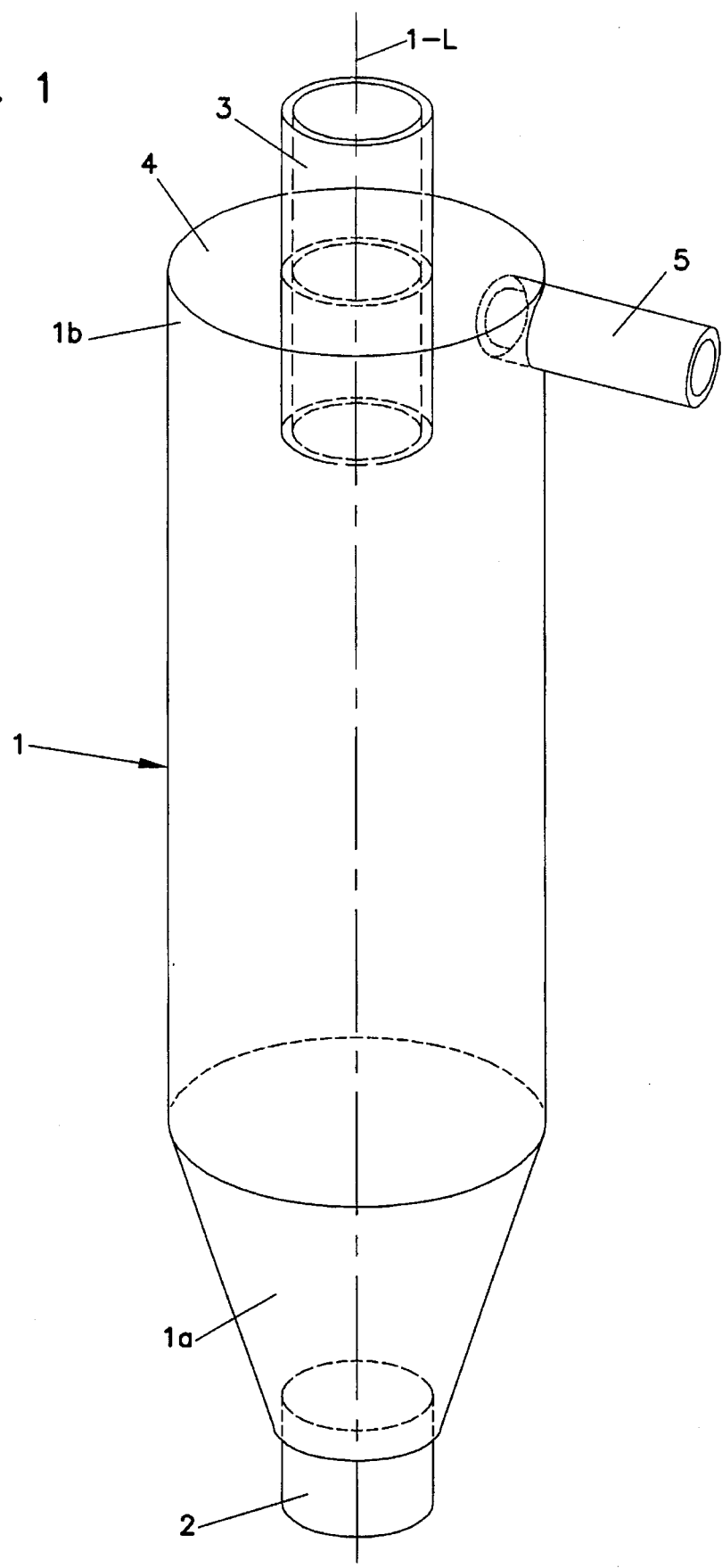

United States Patent [19]

Blaha-Schnabel

[11] Patent Number: 5,596,982
[45] Date of Patent: Jan. 28, 1997

[54] APPARATUS FOR DRYING AND BUFFERING AEROSOLS

[75] Inventor: Ales Blaha-Schnabel, Nürnburg, Germany

[73] Assignee: Paul Ritzau Pari-Werk GmbH, Starnberg, Germany

[21] Appl. No.: 442,582

[22] Filed: May 17, 1995

[30] Foreign Application Priority Data

May 19, 1994 [EP] European Pat. Off. ............. 94107770

[51] Int. Cl.⁶ ................................................. A61M 11/00
[52] U.S. Cl. ................. 128/200.14; 128/200.18; 128/203.15
[58] Field of Search .............. 128/200.14, 200.17, 128/200.18, 203.15, 203.21

[56] References Cited

U.S. PATENT DOCUMENTS

| | | | |
|---|---|---|---|
| 3,362,405 | 1/1968 | Hazel | 128/203.15 |
| 4,429,835 | 2/1984 | Brugger et al. | 239/338 |
| 5,312,046 | 5/1994 | Knoch et al. | 128/200.18 |
| 5,458,135 | 10/1995 | Patton et al. | 128/200.18 |

FOREIGN PATENT DOCUMENTS

| | | |
|---|---|---|
| 504459 | 9/1992 | European Pat. Off. . |
| 8908273 | 9/1989 | Germany . |
| 9015635 | 12/1990 | WIPO . |

*Primary Examiner*—Aaron J. Lewis
*Attorney, Agent, or Firm*—Merchant, Gould, Smith, Edell, Welter & Schmidt, P.A.

[57] ABSTRACT

The apparatus according to the invention for drying and buffering wet aerosols for purposes of inhalation therapy comprises a rotationally symmetric main body, a tubular member arranged on one of the front ends and protruding by a defined length into the main body, and an intake air member through which ambient air can flow into the main body when the patient inhales the aerosol stored in the main body via the other tubular member. In this respect, two spiral turbulences are formed one inside the other, the outer one of which prevents an impaction of the aerosol particles against the inside wall of the vessel.

21 Claims, 4 Drawing Sheets

APPARATUS FOR DRYING AND BUFFERING AEROSOLS

The invention relates to an apparatus for drying and/or buffering aerosols for inhalation therapy.

The inhalation therapy is applied not only for the treatment of diseases of the respiratory tract, but to an increasing degree also for the administration of other medicinal active ingredients for systematic application. In such a therapy, the active ingredient is mixed as a fine mist with air so that it can be inhaled. It is important in this connection that the particles containing the active ingredient be very small (less than 5 μm) in order to ensure that they are carried into the lungs by the respiratory flow and not already deposited in the mouth or pharyngeal cavity. An effective and rapid absorption of the active ingredient only becomes possible in the lungs. Moreover, with certain drugs the deposit of larger particles in the mouth or pharynx can lead to undesirable local side-effects.

"Wet aerosols" are of special significance, and those aerosols are to be understood as being produced by nebulisation of a liquid in which the active ingredient is dissolved or dispersed, possibly together with a carrier substance, for example a salt. Upon the nebulisation of the liquid, fine droplets are formed which have in the initial aerosol, i.e. directly after production of the aerosol with the aid of a nozzle or the like, a size distribution wherein only a certain portion of the droplets is respirable. In order to increase the portion of respirable droplets, the aerosol can be dried so that the size of the individual particles is reduced. This treatment of the initial aerosol substantially contributes to the desired final properties of the aerosol inhaled by the patient. In the case of aerosols on a powder basis, i.e. aerosols which are produced by atomising a pulverous initial substance, the particle size is determined by the initial substance. However, in both types of aerosol, the buffering of a sufficient amount of aerosol is necessary.

In order to support the formation of an aerosol also for the inhalation therapy of the lower respiratory tract, an inhalation vessel of plastic is known from the DE 89 08 273 U1, wherein an inlet and an outlet member are provided on amphora-like main body opposite to each other at the two front faces. On account of the amphora shape, the initial aerosol has the opportunity to spread out and settle, so that a drying also takes place. The known inhalation vessel satisfies the requirements with respect to the buffering, i.e. the preparation of a supply of respirable aerosol. However, by deposit and incomplete emptying of the inhalation vessel, considerable portions of the aerosol, and thus of the drug, become lost.

A further apparatus for the treatment of aerosols is known from the EP 0 504 459 A1; the apparatus comprises a cylindrical nebulisation cavity with a feed member and an exit member which are both respectively arranged tangentially close to one of the front faces on the superficies of the cylindrical nebulisation cavity. By the arrangement of the feed and exit members, a spiral turbulence extending around the longitudinal axis of the nebulisation cavity is generated. This formation can also be supported by a nuclear member which is arranged in the nebulisation cavity coaxially with the cylindrical nebulisation cavity. Alternatively, the feed member can be replaced by a helical surface in the region of the one front face of the nebulisation cavity, which, upon diffuse supply of the initial aerosol, introduces the formation of the spiral turbulence. In the known apparatus, there is a sufficient buffering of respirable aerosol with simultaneous homogenisation and drying. The volume is suitable to be emptied by one breath. However, the aerosol particles tend to deposit on the inner wall of the nebulisation cavity, especially by inertial forces of the wet aerosol directly after exit from the nozzle, or if, upon strong inspiration; the rotational speed is increased and the centrifugal forces are too large. Besides the deposit of the active ingredient occurring on this account, regions are present in the nebuliser from which the aerosol is only incompletely discharged. With these two effects, an objective influencing of the particle size is impossible, or at least rendered considerably difficult.

An apparatus of similar construction is described in the WO 90/15635; however, this apparatus serves for the atomisation of particles of an inhalation drug which is already in pulverous form. The drug is supplied as dry aerosol, namely as fine mist of the particles of powder, to the apparatus. Of primary significance, and thus contrary to the EP 0 504 459 A1, is the generation of a sufficiently large centrifugal force, which effects a further decomposition of the particles and thus an atomisation by impact of the particles against each other and against the inside wall of the nebuliser.

An apparatus known from the U.S. Pat. No. 3,362,405 works according to the same principle with respect to the atomisation, wherein a pulverous substance located on the floor of a cylindrical container is whirled up and by impact of the particles against one another and against the container wall is further pulverized, i.e. atomized. The apparatus serves not only for buffering, but for producing a dry aerosol which is simply administered to the environment. The generation and dispensing take place continuously and are not dependent on a user's breathing. In the known apparatus, the turbulent flow necessary for the centrifugal force is caused in that via a tube arranged tangentially on the superficies of the cylinder, air is blown into the cylindrical container. The whirled up particles of substance are pulverized by impact against each other and against the wall and, together with the air bearing them, leave the cylindrical container through a tube which is provided centrally in the front face of the cylinder, close to which also the members for the intake air are located. The apparatus is similar in construction and function to the basic principle of a separator known as "cyclone", since large particles of the pulverous substance are again deposited.

Whereas the one group of the above described apparatuses are suitable for the treatment of a wet aerosol, the other group of apparatuses must be excluded for this purpose. However, in the apparatuses suitable for treatment of a wet aerosol, improvements are desirable, especially an objective influencing of the size of the aerosol particles. Obviously the improved apparatuses should be suitable for aerosols on a powder basis; furthermore, a deposit of aerosol particles and an impairment of the degree of discharge should be avoided in all kinds of aerosol.

Proceeding from the above described apparatuses, the invention is therefore based on the object of providing an apparatus for drying and/or buffering aerosols, with which the properties of the aerosol, especially the particle size in wet aerosols, can be objectively influenced, wherein the deposit of aerosol particles is avoided, and which can be completely emptied in principle by one breath.

This object is solved by an apparatus for drying and/or buffering aerosols comprising the features of patent claim 1. Advantageous configurations are shown in the subclaims.

The invention advantageously utilizes the two turbulences formed in each other known already from the cyclone separator. This process is explained in more detail in the description of the embodiments. Whereas, however, until now a sufficiently high rotational speed and thus a high centrifugal force was always sought, the apparatus according to the invention essentially distinguishes itself in that on account of the lower speed the outer turbulence effects a shielding which on the one hand prevents the aerosol particles from reaching the vessel wall, and on the other hand rinses the container and thus ensures a very good emptying, i.e. discharge of the aerosol. With the invention an apparatus is proposed for the drying and/or buffering of an aerosol, especially a wet aerosol, which is similar in construction to a cyclone separator, and which by means of the central supply of the aerosol from the one front face and the breath-controlled removal of the aerosol at the other front face of the rotationally symmetric, preferably cylindrical main body with the formation of the two spiral turbulences one inside the other, permits an objective drying of wet aerosols, a depositing on the inside wall being almost entirely avoided.

In a preferred embodiment, the aerosol is produced by a dispersion nozzle which is introduced into a conically tapering part of the cylindrical apparatus. In this nozzle, a solution and/or suspension is mixed with dry air and sprayed axially in the apparat us. The operating parameters of the nozzle, such as dispersion air humidity, dispersion air throughput and bulk liquid flow, are adapted to the dimensions of the apparatus in such a manner that minimal impaction takes place on the opposite end of the apparatus (the air exchange upon filling the vessel corresponds to only about 80% of the volume) and that predetermined average droplet size can be achieved by drying the dispersion air. The total volume of the apparatus is adjusted to the average inspiration volume of a patient so that the apparatus can be emptied in one breath without any problem. Two prefer red embodiments therefore respectively have a volume of 570 ml (for adults) and 350 ml (for 10-year old children) respectively.

In a further preferred embodiment, the solution or suspension which is under pressure is injected in a short thrust through a single-substance nozzle into the apparatus, whereby the air contained in the apparatus is not saturated with solvent (propellant gas) so that a drying can take place. On account of the short spraying thrust, in this case the volume and length of the apparatus can be further reduced or shortened, respectively. This embodiment then has a volume of about 240 ml.

If the patient inhales, via the-undertow which is exerted by an immersion tube in the side of the apparatus lying opposite the nozzle onto the aerosol in the interior, intake air flows into the apparatus from above and is fed in such a manner that cyclone turbulences are generated which run along the vessel wall towards the nozzle. These turbulences urge the aerosol towards the center of the vessel and set the aerosol into a light rotation. The rotating, inner aerosol column is then sucked off through the immersion tube and the apparatus entirely rinsed with further intake air, thus achieving an excellent emptying. Since the bundling and guidance of the aerosol is effected solely by air flows, there is practically no impaction against fixed flow guidance elements which would cause a loss of active ingredient by deposit.

Figure 2:
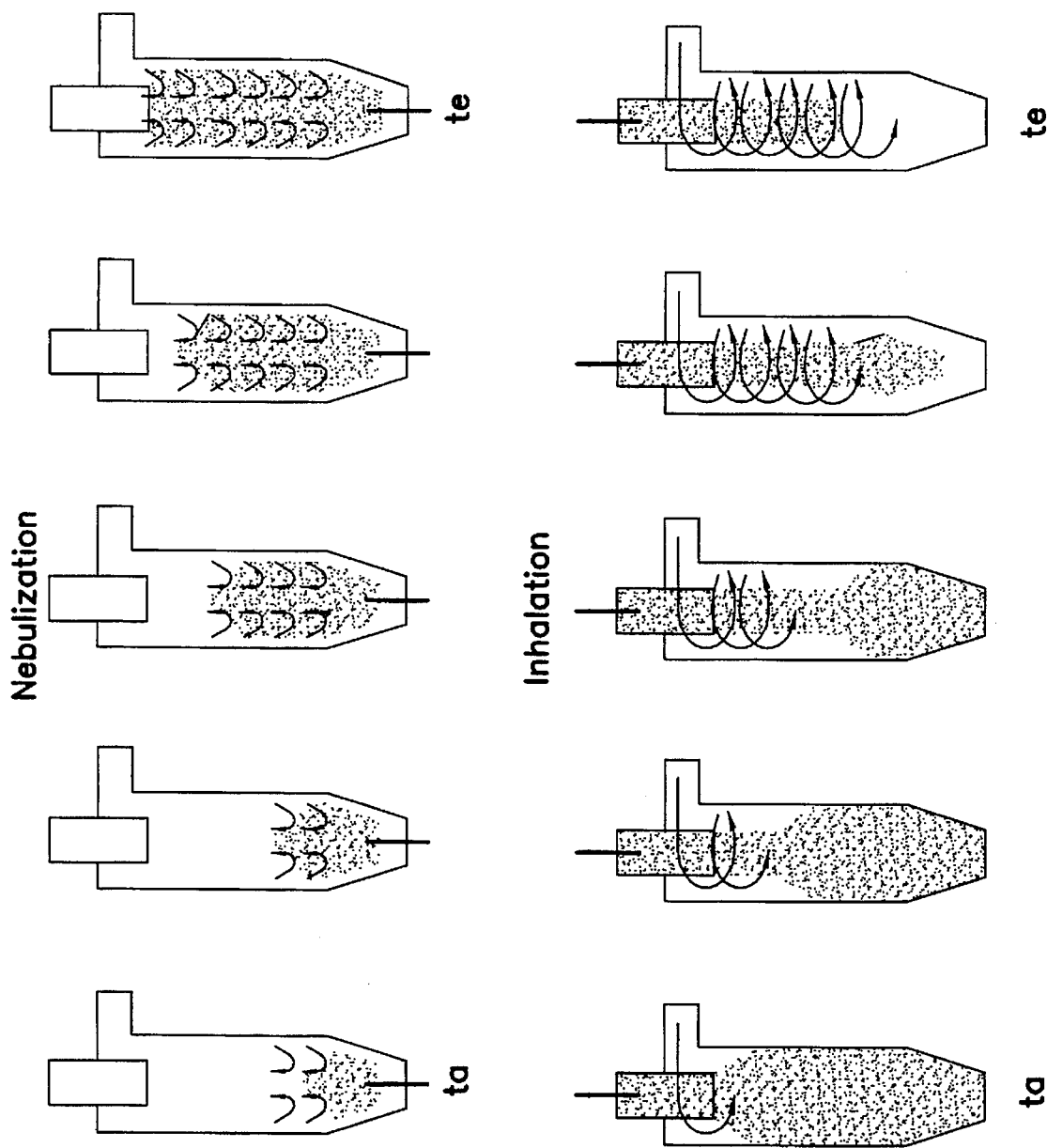
Figure 3:
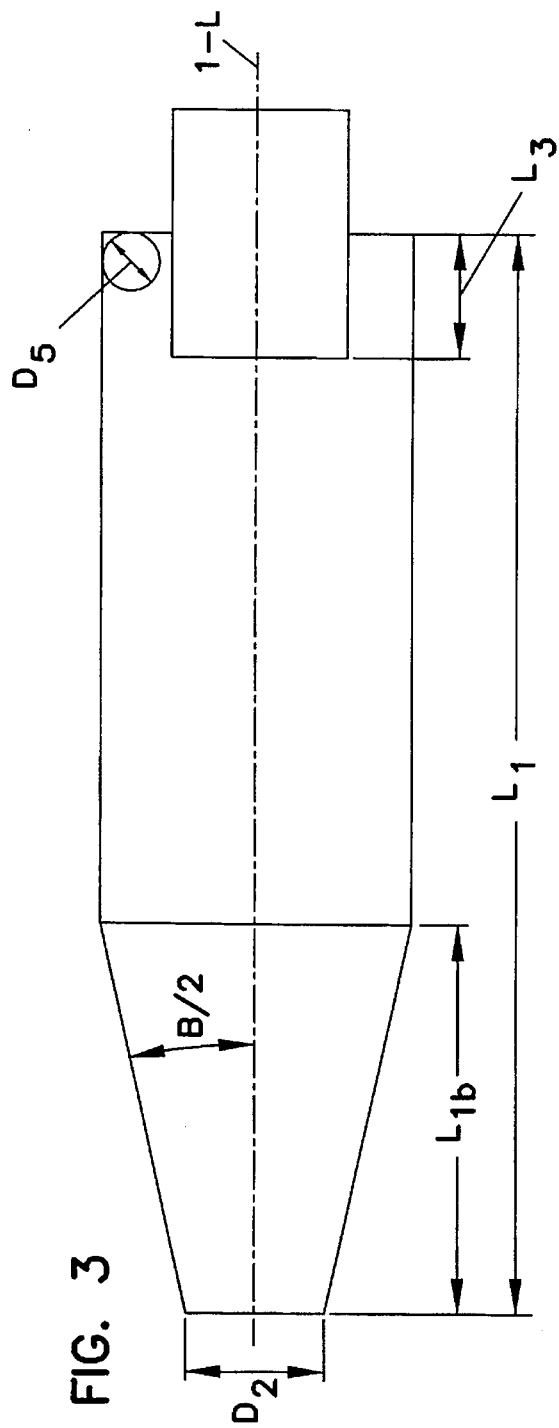
Figure 4:
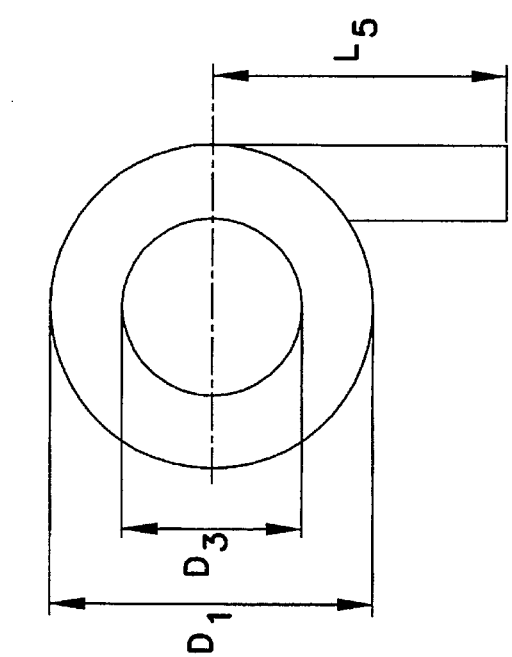
Figure 5:
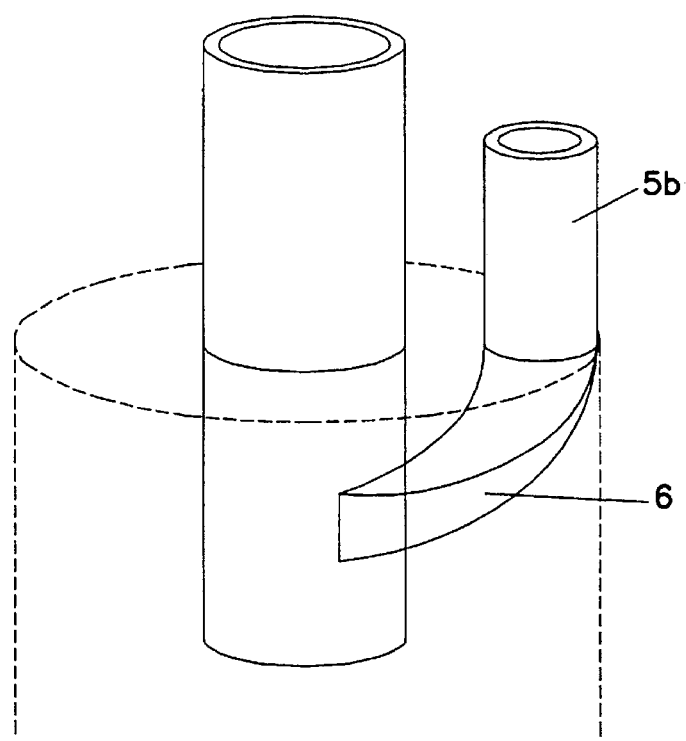
Figure 6:
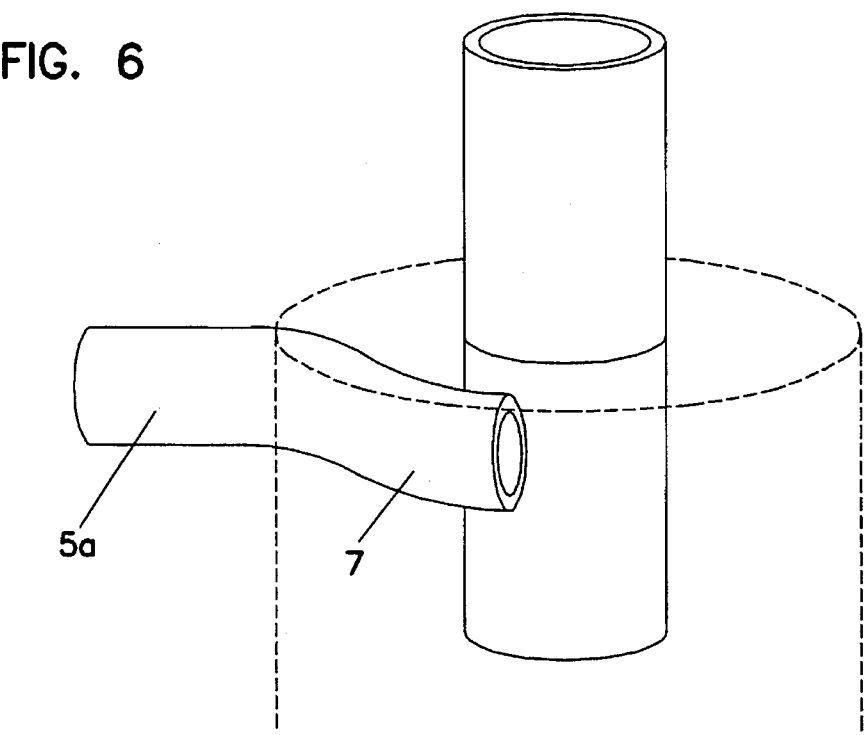

Further details and advantages of the invention can be taken from the description of the embodiments of the apparatus according to the invention represented in the drawings. The drawings show:

FIG. 1 a perspective view of a first embodiment of the apparatus according to the invention equipped with a tangential air supply;

FIG. 2 the flow conditions in the apparatus according to the invention during the nebulisation or expiration process, respectively, by way of example on the first embodiment;

FIG. 3 a longitudinal section through the apparatus of the first embodiment;

FIG. 4 a sectional view of the front end of the first embodiment in the height of the tangential intake air tube;

FIG. 5 a second embodiment, wherein the intake air is supplied via a tube parallel in axis; and FIG. 6 a third embodiment, wherein the intake air is fed radially to the apparatus.

The apparatus represented in FIG. 1 comprises a cylindrical main body 1, which tapers at a first front end in the form of a fulcrum. The smaller aperture of the frustum 1a with a diameter $D_2$ is formed for the connection of a dispersion nozzle 2. The nozzle 2 is sealingly inserted, e.g. with an 0-ring (not shown) and has a direction of injection coaxial to the axis of symmetry 1-L of the cylindrical main body 1. In the second front end 1b of the main body 1, a tubular member 3 is introduced through a hole in the surface 4 closing this front end coaxial to the axis of rotation 1-L of the main body 1, the tubular member 3 protruding by a defined length $L_3$ into the main body 1. Lateral to the second front end 1b of the main body 1, a tangentially opening tubular member 5 is mounted, which serves to feed intake air with the formation of turbulences around the axis of rotation 1-L of the main body 1.

In the dispersion nozzle 2, a drug solution is mixed with dry air and the initial aerosol thus produced centrally sprayed along the axis of symmetry 1-L of the main body 1. FIG. 2 shows how the upwardly directed aerosol jet effects a downward flow of air along the vessel wall. The sum of these flows leads to ring turbulences which have their axis of rotation perpendicular to the axis of symmetry 1-L of the main body 1. These turbulences lead to an efficient distribution of the aerosol and calm it down at the same time, since kinetic energy is drawn from the aerosol particles. The aerosol thus comes into equilibrium and after a short period of time the particles dry down to the desired size. The nozzle 2 is constructed in such a manner that the aerosol close to the immersion tube 3 already flows according to the above described turbulences in order to exclude the impact against the upper end 1b of the main vessel 1 as a result of forces of inertia, so that a deposit of the aerosol at this position is extensively avoided.

When the vessel 1 is filled, i.e. the injection process concluded, the aerosol can be removed via the immersion tube 3. For this purpose, it is favorable to place a mouthpiece (not illustrated) directly onto the immersion tube and to apply this as far as possible as a straight extension of the immersion tube 3 in order to avoid losses by deposit. The immersion tube 3 conveys the pressure reduction occurring due to the removal to the main vessel 1, whereby intake air flows in via the tangential tubular member 5. The tangential supply 5 coupled with the central immersion tube 3, leads to the formation of cyclone turbulences which extend spirally downwards around the axis of rotation of the main body 1 along the vessel wall, as shown in FIG. 2.

On account of this turbulence, the aerosol is compressed towards the center of the vessel 1 to a diameter which corresponds approximately with that of the immersion tube 3, and by means of air friction is set lightly into rotation. On account of the fact that the flow rates effected by inspiration are small in the configuration of the apparatus according to the invention, an excessive centrifugal effect is avoided as described above in the introduction. Simultaneous to the formation of the cyclone turbulence, the rotating aerosol column is suctioned through the immersion tube 3 and the dryer vessel 1 finally rinsed with following intake air. Thereafter aerosol can be sprayed in anew and a new inhalation cycle can commence.

The apparatus can be operated in all spatial positions as long as filling and expiration take place in close succession (sedimentation of particles negligible).

In FIG. 3 and 4, and in the following tables, expedient dimensions of the embodiment represented in FIG. 1 are shown.

| Nr. | B [°] | $D_1$ [mm] | $L_1$ [mm] | $D_3$ [mm] | $L_3$ [mm] | $D_5$ [mm] | $L_5$ [mm] | $L_{1b}$ [mm] | $D_2$ [mm] | V [ml] |
|---|---|---|---|---|---|---|---|---|---|---|
| 1 | 28 | 54 | 180 | 30 | 20 | 10 | 50 | 65 | 22 | 350 |
| 2 | 28 | 64 | 210 | 40 | 25 | 10 | 50 | 85 | 22 | 570 |
| 3 | 28 | 64 | 120 | 40 | 25 | 10 | 50 | 85 | 22 | 240 |

In general, the diameter $D_5$ of the intake air tube 5 should be preferably selected in such a manner that the sum of the diameter $D_3$ of the immersion tube and twice the inside diameter $D_5$ of the intake air tube is approximately the same as the diameter $D_1$ of the dryer vessel 1. In other words, the aperture diameter $D_5$ of the intake air tube 5 should extensively utilize the width available beside the immersion tube 3. Then, namely, the circular flow around the immersion tube 3 takes place without any broadening or narrowing of the air flow entering from the intake member 5, which favors an optimum flow and discharge. Furthermore, it is advantageous to select the length $L_3$ of the immersion tube 3 protruding into the dryer to be as large as the diameter $D_5$ of the intake tube 5 to ensure specially good formation of the cyclone turbulence. The immersion tube 3 should not be selected to be longer, since otherwise during the injection process, aerosol would precipitate in and-on the immersion tube 5 due to increased impaction.

The total volume of the apparatus should preferably be optimized to the tidal-volume of a group of patients so that it can be entirely emptied as far as possible in one breath. On the basis of the empirically determined average tidal volume of 750 ml for adults and 450 ml for approximately 10-year old children, a preferred embodiment for adults has a total volume of 570 ml and a further embodiment for children a volume of 350 ml.

For the spacer volume calculation, a 20 to 30% reduction from the respective inspiration volume is considered so that the mouth cavity and the upper respiratory tract, in which the aerosol cannot achieve any effect, can be rinsed out with fresh air (e.g. 200 ml for adults).

In the embodiment described until now, the intake air is supplied via a straight, tangentially opening tubular member 5. By means of the direct supply without any deflection means, a minimum flow resistance is achieved which is very important in the case of patients with a weakness of the lungs, since this resistance needs to be overcome during inhalation. However, other embodiments are also conceivable. In order to save space, namely, the intake air conduit could also be conducted in a circular manner on the outer wall of the second front end 1b (not shown), or also a tubular member 5b opening parallel in axis from above could be selected, as shown in FIG. 5. However, in the latter case, a deflection means increasing the flow resistance would need to be added to produce a tangential flow. In FIG. 5 shovel-like guide surface 6 is shown. Finally, a radial introduction of intake air 5a is also conceivable, such as shown in FIG. 6, with an adapted deflection means 7 for generating a tangential flow.

Independent of the specific configurations of the conducting of intake air, it is advantageous to apply an inspiration valve (not show) on the end of the intake air tube opposite to the opening of the housing in order to prevent air from flowing out of the main vessel 1 in this way. A sufficient length of the intake air conductance is then important so that the turbulent flow caused by the valve can be steadied again before entering the vessel 1. A strong turbulence when flowing in, or an asymmetrical flow profile, would reduce the efficiency of the apparatus, since the formation of cyclone turbulences would be unfavorably influenced and the flow resistance unnecessarily increased.

The conical tapering of the first front end 1a of the main vessel 1, which is represented in FIG. 1 and 3, serves to avoid clearance volumes in which aerosol could accumulate without being discharged. The cylindrical shape of the main body 1 in the embodiments is the simplest form permitting the formation of cyclone turbulences upon tangential air supply. However, other rotationally symmetrical main bodies are also conceivable, for example a totally conical tapering from one end 1a to the other end 1b (not shown). In this case, the entire vessel (main body 1 and end 1a) would have the shape of a frustum.

Since due to the friction of the flowing air on the vessel wall of the apparatus, an electrostatic charging of the wall can take place, it is advantageous to manufacture the vessel from an antistatically effective substance. The attracting forces caused by the charging would effect an increased deposit of aerosol particles on the vessel wall, which would mean a loss of drug. A lining of the vessel inside wall with an antistatic coating is also conceivable.

Finally, an advantageous embodiment of the apparatus shown in FIG. 1 consists in manufacturing the cylindrical main body 1, the cortically tapering member 1a and the opposite end 1b containing the immersion tube 3 and the intake air tube 5 as separate members which are releasably connected to each other, e.g. by simple plugging. This simplifies not only the manufacture of the apparatus, but also simplifies cleaning and disinfection thereof. Moreover, a variation of the size would also be possible, for example by inserting a shortened cylindrical intermediate member, which would permit a use of the apparatus as compact inhalation aid for dosage aerosols produced with a propellant gas.

I claim:

1. An apparatus for drying and/or buffering aerosols for purposes of inhalation therapy, comprising:

a main body having rotational symmetry about a first longitudinal axis, the main body comprising a wall defining an inner surface, the main body having first and second ends, the first end of the main body being tapered for connection to an outlet of an aerosol generator, the second end of the main body being closed with a surface;

a first tubular member extending through the surface closing the second end of the main body, having a longitudinal axis that is disposed parallel to the longitudinal axis of the axis of rotation of the main body, protruding by a defined length into the main body from the second end; and an intake member separate from said first tubular member for supplying intake air into the main body to form turbulence around the axis of rotation of the main body.

2. An apparatus according to claim 1, wherein the first tubular member is disposed centrally in the surface closing the second end of the main body.

3. An apparatus according to claim 1, wherein the intake member is a second tubular member opening tangentially into the main body.

4. An apparatus according to claim 3, wherein the second tubular member opening tangentially into the main body is disposed directly beneath the surface closing the second end of the main body.

5. An apparatus according to claim 4, wherein the length by which the first tubular member protrudes into the main body is approximately twice as large as the diameter of the second tubular member.

6. An apparatus according to claim 3, wherein the sum of twice the diameter of the second tubular member plus the diameter of the first tubular member is approximately equal to the diameter of the main body.

7. An apparatus according to claim 6, wherein the length by which the first tubular member protrudes into the main body is approximately twice as large as the diameter of the second tubular member.

8. An apparatus according to claim 3, wherein the length by which the first tubular member protrudes into the main body is approximately twice as large as the diameter of the second tubular member.

9. An apparatus according to claim 1, wherein the intake member is a third tubular member that opens radially into the main body, the apparatus further comprising a deflector connected to the third tubular member to generate a tangential flow in the intake air.

10. An apparatus according to claim 1, wherein the intake member is a fourth tubular member that opens into the main body in a direction parallel to the longitudinal axis of the main body, the apparatus further comprising a deflector connected to the fourth tubular member to generate a tangential flow in the intake air.

11. An apparatus according to claim 1, further comprising an atomizer having a nozzle for injecting aerosol into the main body through the first end, the direction of injection being aligned parallel to the longitudinal axis of the main body.

12. The apparatus according to claim 1, wherein the tapering first end is formed in the shape of a frustum.

13. The apparatus according to claim 1, wherein the main body has a volume of approximately 570 ml, approximately 350 ml, or approximately 240 ml.

14. An apparatus according to claim 1, wherein the intake member has a second end facing away from the main body, the second end of the intake member being connected to a valve.

15. An apparatus according to claim 1, wherein the first tubular member has a second end facing away from the main body, the second end of the first tubular member being closed with a valve to which a mouthpiece is connected.

16. The apparatus according to claim 1, wherein the material and surface of the main body are selected so that the inner surfaces of the main body are anti-static.

17. An apparatus according to claim 1, wherein the first end and the second end are defined by separate members that can be releaseably connected with the main body.

18. An apparatus for drying and/or buffering aerosols for purposes of inhalation therapy comprising:

a main body that is rotationally symmetric about a longitudinal axis, the main body having a first end that is tapered and suitable for connection to an aerosol generator, the second end of the main body being closed with a surface;

a first tubular member extending through a surface closing the second end of the main body and extending into the main body so that an inlet of the first tubular member is in the vicinity of the second end of the main body; and an intake member separate from said first tubular member for the supply of intake air into the main body, the intake member being disposed in the vicinity of the second end of the main body, whereby upon inhalation through the first tubular member intake air flows into the main body through the intake member and forms a cyclone turbulence in the main body that extends downwards toward the first end of the main body, thereby forcing aerosol in the main body toward the center of the main body.

19. The apparatus of claim 18, wherein the intake member is a second tubular member opening into the main body.

20. The apparatus of claim 19, wherein the sum of twice the diameter of the second tubular member plus the diameter of the first tubular member is approximately equal to the diameter of the main body.

21. An apparatus according to claim 19, wherein the first tubular member protrudes into the main body a length that is approximately twice as large as the diameter of the second tubular member.

* * * * *